United States Patent [19]

Gradeff

[11] 4,152,530

[45] May 1, 1979

[54] PROCESS FOR PREPARING ALLYLIC ALCOHOLS FROM ALLYLIC HALIDES

[75] Inventor: Peter S. Gradeff, Andover, N.J.

[73] Assignee: Rhone-Poulenc Inc., New York, N.Y.

[21] Appl. No.: 927,330

[22] Filed: Jul. 24, 1978

[51] Int. Cl.² .................. C07C 33/02; C07C 29/00
[52] U.S. Cl. ................................. 568/875; 568/877
[58] Field of Search ...................... 568/877; 568/875

[56]     References Cited
         U.S. PATENT DOCUMENTS

| 2,833,811 | 5/1958 | Surmatis .............................. 568/877 |
| 3,968,177 | 7/1976 | Kaufhold et al. ..................... 568/877 |

FOREIGN PATENT DOCUMENTS

| 119249 | 10/1918 | United Kingdom ..................... 568/877 |
| 979523 | 1/1965 | United Kingdom ..................... 568/875 |

*Primary Examiner*—Joseph E. Evans

[57]          ABSTRACT

A process for preparing allylic alcohols from allylic halides is provided by way of the intermediate formation of an ester in the presence of a water-insoluble ketone forming an azeotrope in water followed by saponification of the ester with alkali metal hydroxide, drying the alkali metal carboxylic acid salt formed during the saponification by azeotropic distillatiion with the ketone, thus obviating expensive separate recovery facilities and handling of the dried alkali metal carboxyolate salt. The overall process amounts to a hydrolysis of the allylic halide with aqueous alkali metal hydroxide and one reactor can serve for the whole process.

23 Claims, No Drawings

PROCESS FOR PREPARING ALLYLIC ALCOHOLS FROM ALLYLIC HALIDES

Allylic halides including terpene allylic halides are available from various sources, and are valuable intermediates in the preparation of allylic esters and alcohols which are useful as perfumery ingredients and flavors. Terpene allylic halides such as myrcene hydrohalides are a source of geraniol and linalol, while allylic alcohols of the spearmint series may be obtained from carvyl chloride, and allylic alcohols of the peppermint series from 5-chloro-3-menthene.

Webb U.S. Pat. No. 3,031,442, patented Apr. 24, 1962, reacts an allylic terpene halide with a salt of a carboxylic acid in the presence of a nitrogen base catalyst, or its salt, which also acts as a catalyst. No solvent is required, except to facilitate agitation of the halide with a solid salt. Any inert hydrocarbon solvent such as naphthas, lower aromatics or saturated halide solvents are suitable as would be ethers, ketones, lower fatty acids corresponding to the ester desired, etc. The lower fatty acids are not truly inert solvents, however, as large proportions depress the catalyst activity to the extent shown by the examples. The product of the reaction is a terpenic ester, which can be hydrolyzed to the corresponding terpenic allylic alcohol. Webb indicates that any carboxylic acid salt will serve, and that sodium acetate is generally preferred.

Webb U.S. Pat. No. 3,280,177, patented Oct. 18, 1966, provides a variation in which the reaction of the allylic terpenic halide with the carboxylic acid salt is catalyzed by the presence of dimethyl sulfoxide, which acts as a solvent catalyst.

BASF Aktiengesellschaft British Pat. No. 1,459,622, published Dec. 22, 1976, suggests that the results obtained by Webb can be improved if the reaction between the terpenic allylic halide and the nitrogen-containing catalyst is carried out in the presence, as cocatalyst, of a polar aprotic compound which has a dipole moment of at least 3.1 Debye, a dielectric constant of more than 15, and a melting point of less than 60° C., and/or of an ionic iodide. The polar aprotic compounds are said to have only a slight catalytic effect when used alone, but considerably enhance the catalytic effect of the basic nitrogen compound. The polar aprotic compounds include N,N-dialkylamides, sulfoxides, sulfones, nitriles, nitro compounds, carbonates, phosphoric esters, and phosphonamides.

French Demande de brevet d'invention No. 74.16029 published Dec. 6, 1974 has a similar disclosure, with an expanded disclosure of polar aprotic compounds including ketones and amides. Examples include acetone.

Japanese published unexamined patent application No. 10207/1977, published Jan. 26, 1977 describes a process for preparing 3-methyl-2-butene-1-ol by reacting 1-chloro-3-methyl-2-butene with a carboxylic acid salt in the presence of a nitrogen-containing base or a phosphorus-containing base to form the corresponding ester, and then hydrolyzing the ester to obtain the 3-methyl-2-butene-1-ol. The reaction is carried out in two stages, with isolation of the intermediate ester, separating it from unreacted carboxylic acid salt, and the corresponding common salt, at the completion of the esterification reaction. The solution of ester and unreacted allylic chloride is combined with aqueous sodium hydroxide solution, and then hydrolyzed to the allylic alcohol.

All of these processes have a common problem, and that is, disposal of the alkali metal carboxylic acid salt after the hydrolysis reaction. Discarding the alkali carboxylate salt solution and starting new batch with fresh supply of salt is feasible, but economically unattractive. Besides the direct cost of the salt, which is relatively high, there are problems associated with discarding the solution. How to recover the salt by evaporation of its aqueous solutions is well known. To build the necessary installation for this recovery is expensive, and operation requires labor in handling the solid salt that is recovered.

The proposed process accomplishes the recycling of the salt economically as an integral part of a cyclic process, each cycle of which can be carried out in the same reactor.

In accordance with the invention, a cyclic process is provided for preparing allylic alcohols from allylic halides via an intermediate ester which makes it unnecessary to isolate the ester, and realizes the regeneration of the carboxylic acid salt in the same equipment, in a manner obviating costly alternate drying procedures that require special installations and handling operations. The result is that the allylic halide can be converted to allylic alcohol in a minimum of steps, and the only reagent is an aqueous solution of alkali metal hydroxide.

The process of the invention comprises:

(1) esterifying an allylic halide having the formula:

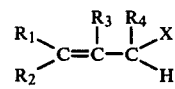

wherein:

(a) $R_1$, $R_2$, $R_3$ and $R_4$ are selected from the group consisting of hydrogen and alkyl;

(b) one of $R_1$ and $R_2$ has from one to about twenty carbon atoms, the remaining one of $R_1$ and $R_2$, $R_3$ and $R_4$ having from one to about five carbon atoms, and (c) X is halogen selected from the group consisting of chlorine, bromine and iodine, at a temperature within the range from about 50° to about 150° C., under anhydrous conditions and in the presence of a basic nitrogen-containing catalyst with an alkali metal carboxylic acid salt, the allylic halide being in solution in a water-insoluble ketone forming an azeotrope with water, thereby forming an ester of the allylic halide and the carboxylic acid, and an alkali metal halide;

(2) adding water to dissolve the alkali metal halide and then discarding the alkali metal halide aqueous solution;

(3) adding aqueous alkali metal hydroxide to the reaction mixture in an amount to hydrolyze the allylic ester, forming aqueous and organic phases and then heating the reaction mixture at a temperature within the range from about 50° to about 150° C. until allylic alcohol is formed;

(4) separating the aqueous and the organic phases;

(5) distilling off the allylic alcohol from the organic phase; and optionally recycling the ketone that remains;

(6) adding ketone to the aqueous layer from (4) and azeotropically distilling off the water from the aqueous phase, and forming anhydrous alkali metal carboxylic acid salt as a slurry in the ketone; and (7) recycling the recovered alkali metal carboxylic acid salt and ketone to step (1).

The allylic alcohol is separated from the ketone solvent by distillation, and can be recovered in substantially pure condition, free from unreacted materials. There are substantially no side reactions in both steps. Hence, very high yields of allylic alcohol from the allylic halide are obtainable.

The class of allylic halides to which the invention is applicable includes open chain allylic type halides including aliphatic allylic halides. Exemplary allylic halides include 1-chloro-3-methyl-2-butene; 1-chloro-3,7-dimethyl-octa-2,6-diene; and 1-chloro-3,7,11-trimethyl-dodecyl-2,6,10-triene.

The alkali metal carboxylic acid salt is preferably a salt of an aliphatic or aromatic carboxylic acid having from one to about five carbon atoms, such as acetic acid, formic acid, propionic acid, butyric acid, and valeric acid; maleic acid; oxalic acid; tartaric acid; gluconic acid; citric acid; succinic acid; malic acid; benzoic acid; terephthalic acid. The alkali metals include sodium and potassium. Preferred salts are sodium acetate and potassium acetate.

The basic nitrogen compound catalyst is known, and forms no part of the instant invention. It can be any of the catalysts referred to by Webb in U.S. Pat. No. 3,031,442, column 3, lines 32 to 70, including ammonia, amines, amidines, amides, oximes, hydroxylamines, hydrazones, semicarbazides, and imines, and salts thereof. The amines can be primary, secondary or tertiary, and alkyl, aryl or heterocyclic.

The preferred nitrogen bases are tertiary amines, such as trimethylamine, triethylamine, triethanolamine, tripropylamine, and tributylamine.

The ketone employed as a solvent for the esterification stage and which remains in the organic layer during the hydrolysis stage can be any water-insoluble ketone which forms an azeotrope with water. Water-soluble lower ketones such as acetone and methyl ethyl ketone do not form azeotropes with water and do not fulfill this function. Water-insoluble aliphatic higher ketones that can be used include diisobutyl ketone, 3-pentanone, methyl hexyl ketone, 2-heptanone, and methyl heptenone. Water-insoluble aromatic ketones that can be used include benzophenone and acetophenone. Of the cycloaliphatic ketones isophorone can be given as an example. If the metal carboxylate used forms a hydrate, then the ketone that is selected should have a boiling point above the decomposition temperature of the hydrate.

The concentration of ester or halide in the ketone is not critical. Enough ketone should be present to given an easily agitated reaction mixture. The ketone added to the aqueous phase azeotropically distills off the water. The amount of ketone used in the condensation step need not be the same as the amount used in the azeotropic distillation of the water and these ratios can vary.

In many cases, an unduly large amount of ketone can retard the rate of hydrolysis. Therefore, during the condensation and hydrolysis steps the amount of ketone should be within the range from 100 to 200 ml per mole of allylic ester or halide. Ketone can be removed if more than this remains after the azeotropic distillation of the water.

The process of the invention can be carried out in one reaction vessel from which the alkali metal carboxylic acid salt is never removed. The reaction vessel can be used, in sequence, for the esterification, the hydrolysis and the drying stages of the reaction. After azeotropic distillation of the water, the alkali metal carboxylic acid salt is dry and ready for the next cycle. The esterification can be carried out upon addition of the allylic halide and the amine catalyst to the reaction vessel.

The esterification reaction is carried out at a temperature within the range from about 50° to about 150° C., and is generally complete within a manner of minutes or hours, ranging from minutes up to about 10 hours. At from 90° to 130° C., the reaction is complete within from one to two hours. The reaction time is inversely proportional to the reaction temperature, and shorter reaction times are needed at the higher reaction temperatures.

Inasmuch as the alkali metal carboxylic acid salt reacts with the allylic halide, equimolar, i.e., 1:1, stoichiometric proportions are required. A slight excess of the salt, of the order of from 5 to 20% in excess of the molar amount, is normally desirable, to drive the reaction further towards completion. Thus, the molar ratio of allylic halide:carboxylate salt is generally within the range from about 1:1 to about 1:1.2.

The basic nitrogen compound catalyst is effective in rather small amounts. An amount as small as 0.25 mole percent, based on the allylic halide, can be used. Better results are obtained at amounts within the range from about 1 to about 10 mole percent, but even larger amounts, up to about 20 mole percent, can be used, if desired.

When esterification is complete, water is added sufficient to dissolve the resulting alkali metal halide salt, and the aqueous alkali metal halide solution removed and discarded. The ketone phase can then be subjected to hydrolysis.

The hydrolysis can be begun at once by addition of aqueous alkali. In the hydrolysis stage of the reaction, at least a stoichiometric amount of alkali is required. A slight excess of alkali can be used. The molar ratio ester:alkali can be from 1:1 to 1:1.1.

The alkali can be any alkali metal hydroxide, such as sodium and potassium hydroxide.

The alkali metal hydroxide is used as an aqueous solution. While the concentration is not critical, concentrated solutions such as from 20% to 50% alkali are preferred as there will be less water to remove during the regeneration of the alkali metal carboxylic acid salt.

The hydrolysis reaction proceeds at an elevated temperature within the range from about 50° to about 150° C., preferably from about 75° to about 125° C. Quantitative yields are obtainable.

The allylic alcohol is formed in a relatively short time. The reaction is usually complete within the range from about 0.5 to about 10 hours. At from 110° to 120° C., about ¾ hour to 1½ hours is sufficient. Again, however, the reaction time depends to some extent upon reaction temperature, and decreases as the temperature increases.

At the conclusion of the hydrolysis stage, the aqueous phase contains the alkali metal carboxylic acid salt, and unreacted alkali metal hydroxide, depending on the excess used. The ketone phase contains the allylic alcohol, most of the ketone, and unreacted materials, including any ester and allylic halide. To separate these components, the ketone phase is decanted from the aqueous phase, and distilled out. If the ketone and the amine having boiling points sufficiently spaced from the boiling point of the allylic alcohol, they can be separated by fractional distillation.

Before working up the aqueous phase, any unreacted alkali metal hydroxide should be neutralized. Although any carboxylic acid can be used, it is preferable to use the acid of the carboxylic acid salt employed in the esterification step.

After adding as much ketone as required to azeotropically distill off the water, the azeotropic distillation is carried out, using a water trap, until no more water separates. The anhydrous salt is then ready for reuse for a new esterification reaction. If the same vessel is used throughout, it can be used in situ in the vessel.

The following Examples in the option of the inventor represent preferred embodiments of the invention:

EXAMPLE 1

Into a one liter three-neck flask equipped with a condenser, mechanical stirrer, thermometer, and dry-ice trap was charged sodium acetate 180.5 g 2.2 moles, diisobutyl ketone 161.6 g 100 ml/mole, and 1-chloro-3-methyl-2-butene, 218.8 g, 2.0 moles, with stirring. The mixture was heated to reflux, and 1.0 g triethylamine added. The reaction was allowed to proceed while monitoring the amount of 1-chloro-3-methyl-2-butene by gas-liquid chromatographic analysis. When the reaction was 95% complete, another 1.0 g of triethylamine was added. When the reaction was about 99.5% complete, 340 ml of water was added. The aqueous layer was then separated at above 80° C., and discarded. The ketone layer was then heated to about 120° C., whereupon 33.93% aqueous NaOH 208.7 grams (2.05 moles) was charged in about twenty minutes, keeping the pot at reflux throughout the addition. Refluxing was continued for an additional hour, at which time sampling showed virtually quantitative hydrolysis to 3-methyl-1-butanol. The organic layer was separated at 80°–90° C.; it weighed 327.8 grams (333.8 grams theory).

The ketone layer was transferred into a 500 ml distilling flask, and distilled under reduced pressure, initially at 130 mm, and 25° C., gradually increasing both temperature and vacuum to 2.5 mm at 77° C. vapor temperature, 108° C. pot temperature. Gas-liquid chromatographic analysis of the distillate showed:

| Product | % | Weight |
|---|---|---|
| 3-Methyl-1-butanol | 49.7% | 156.2 g |
| 3-Methyl-3-butanol | 1.1% | 3.5 g |
| 2,4-Dichloro-2-methyl-butane | 0.9% | 2.8 g |
| Diisobutyl ketone | 39.0% | 122.6 g |
| Yield based on 1-chloro-3-methyl-2-butene=90.5% | | |

The aqueous layer 290 g was then heated to 90° C., neutralized to a pH of 7.5 with glacial acetic acid, diisobutyl ketone added, and the $H_2O$/diisobutyl ketone azeotrope distilled off. The water was collected and the ketone returned to the pot. When water ceased to distil, the amount of ketone was adjusted to 100 ml/mole and a new cycle begun by adding 1-chloro-3-methyl-butene-2 218.8 g. 2.0 moles. The mixture was stirred and heated to 115° C., and then 1.0 g triethylamine was added. When the reaction was 95% complete another 1.0 g triethylamine was added. When the reaction was about 99.5% complete, it was quenched with 340 ml $H_2O$ and worked up as before.

The ketone layer was hydrolyzed as before, and 236 g 3-methyl-1-butanol recovered.

EXAMPLES 2 to 5

Using the procedure of Example 1, substituting the alkali metal carboxylate salt/alkali metal hydroxide or the ketone shown in Table I and under the conditions shown in the Table the indicated allylic halide was converted to the corresponding alcohol in good yield.

TABLE I

| | | | A. CONDENSATION | | | | | | | B. HYDROLYSIS | | | | | C. Azeotropic distillation and recovery of the anhydrous Carboxylic Acid Salt** | | | Allylic |
|---|---|---|---|---|---|---|---|---|---|---|---|---|---|---|---|---|---|---|
| Ex. No. | Carboxylic Acid Salt* | Allylic Halide | ml | Ketone | Amine catalyst ml | g. | Temp °C. | Time Hrs. | % Unreacted Halide | Base | mol | Water g. | Temp. °C. | Time Hrs. | Ketone | ml | Temp. °C. | Alcohol obtained | Yield % |
| 2 | Na Formate | 1-Cl-3-Me-2-butene 1.1 | 100 | aceto-phenone | 1.0 | 3 | 90-95 | 4.0 | 2.7 | NaOH | 1.1 | 102 | 100 | 2 | aceto-phenone | 200 | 110-130 | 3-Me-2-butene-1-ol | 89 |
| 3 | K acetate | 1-Cl-3-Me-2-butene 1.1 | 100 | aceto-phenone | 1.0 | 1 | 100 | 1.5 | 0.1 | KOH | 1.1 | 62 | 100 | 2 | aceto-phenone | 150 | 110-120 | 3-Me-2-butene-1-ol | 98 |
| 4 | Na acetate | 1-Cl-3-Me-2-butene 5.5 | 928 | methyl hexyl-ketone | 5.0 | 5 | 80 | 11 | 0.2 | NaOH | 5.5 | 1320 | 110 | 2 | methyl hexyl ketone | 700 | 110-125 | 3-Me-2-butene-1-ol | 95 |
| 5 | K acetate | Geranyl + nerylchloride 1.2 | 100 | aceto-phenone | 1.0 | 3 | 100 | 6 | 1.0 | KOH | 1.1 | 62 | 110 | 2 | aceto-phenone | 150 | 105-120 | Geraniol and nerol | 90 |

*in a series of reactions the carboxylic acid salt used is the one recovered in C

**prior to drying, the excess of base in B is neutralized with the corresponding carboxylic acid Having regard to the foregoing disclosure, the following is claimed as the inventive and patentable embodiments thereof:

1. A cyclic process for preparing allylic alcohols from allylic halides and carboxylate salts via an intermediate allylic ester without isolation of the ester, and with concurrent regeneration of the carboxylate salt in the course of the process, in anhydrous condition for recycling to the esterification, comprising:

(1) esterifying an allylic halide having the formula:

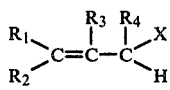

wherein:
(a) $R_1$, $R_2$, $R_3$ and $R_4$ are selected from the group consisting of hydrogen and alkyl;
(b) one of $R_1$ and $R_2$ has from one to about twenty carbon atoms, the remaining one of $R_1$ and $R_2$, $R_3$ and $R_4$ having from one to about five carbon atoms, and
(c) X is halogen selected from the group consisting of chlorine, bromine, and iodine, at a temperature within the range from about 50° to about 150° C. under anhydrous conditions and in the presence of a basic nitrogen-containing catalyst with an alkali metal carboxylic acid salt, the allylic halide being in solution in a water-insoluble ketone forming an azeotrope with water, thereby forming an ester of the allylic halide and the carboxylic acid, and an alkali metal halide of the carboxylic acid salt;

(2) adding water to dissolve the alkali metal halide and then discarding the alkali metal halide;

(3) adding aqueous alkali metal hydroxide to the reaction mixture in an amount sufficient to hydrolyze the allylic ester, forming aqueous and organic phases and then heating the reaction mixture at a temperature within the range from about 50° to about 150° C. until allylic alcohol is formed;

(4) separating the aqueous and ketone phases;

(5) distilling off allylic alcohol from the organic phase;

(6) adding ketone to the aqueous layer from (4) and azeotropically distilling off the water, thus forming anhydrous alkali metal carboxylic acid salt as a slurry in the ketone; and (7) recycling the recovered alkali metal carboxylic acid salt and ketone to step (1).

2. A process according to claim 1 in which the aqueous phase from step (4) is neutralized to take up unreacted alkali metal hydroxide before azeotropic removal of the water, by addition of the corresponding carboxylic acid.

3. A process according to claim 1 which comprises recycling the ketone residue from step (5) to the azeotropic distillation in step (6).

4. A process according to claim 1 in which the allylic halide is an aliphatic allylic halide.

5. A process according to claim 4 in which the allylic halide is an aliphatic allylic chloride.

6. A process according to claim 1 in which the allylic halide is 1-chloro-3-methyl-2-butene.

7. A process according to claim 1 in which the allylic halide is 1-chloro-3,7-dimethyl-octa-2,6-diene.

8. A process according to claim 1 in which the allylic halide is 1-chloro-3,7,11-trimethyl-dodecyl-2,6,10-triene.

9. A process according to claim 1 in which the allylic halide is linalyl chloride.

10. A process according to claim 1 in which the allylic halide is geranyl chloride.

11. A process according to claim 1 in which the alkali metal carboxylic acid salt is a salt of an aliphatic or aromatic carboxylic acid having from one to about ten carbon atoms.

12. A process according to claim 11 in which the salt is sodium acetate.

13. A process according to claim 11 in which the salt is potassium acetate.

14. A process according to claim 11 in which the salt is sodium formate.

15. A process according to claim 1 in which the basic nitrogen-containing catalyst is selected from the group consisting of ammonia, amines, amidines, amides, oximes, hydroxylamines, hydrazones, semicarbazides, imines and salts thereof.

16. A process according to claim 1 in which the ketone is selected from the group consisting of aliphatic and aromatic ketones.

17. A process according to claim 1, carried out in one reaction vessel from which the alkali metal carboxylate salt is never removed, the vessel being used, in sequence, for the esterification and the hydrolysis stages of the reaction; the anhydrous alkali metal carboxylate salt remaining after azeotropic distillation of water and ketones being left in the reaction vessel and the next esterification being carried out simply by addition thereto of the allylic halide and ketone.

18. A process according to claim 1 in which the esterification is carried out at a temperature within the range from about 90° to about 130° C.

19. A process according to claim 1 in which the molar ratio of allyl halide:carboxylate salt is within the range from about 1:1 to about 1:1.2.

20. A process according to claim 1 in which the basic nitrogen-containing catalyst is in an amount within the range from about 1 to about 20 mole percent.

21. A process according to claim 1 in which the hydrolysis is effected by aqueous alkali, and the molar ratio ester:alkali is from 1:1 to 1:1.1.

22. A process according to claim 21 in which the aqueous alkali contains from 20% to 50% alkali.

23. A process according to claim 1 in which the hydrolysis reaction is carried out at a temperature within the range from about 75° to about 125° C.

* * * * *